United States Patent [19]

Parker

[11] 4,110,351
[45] Aug. 29, 1978

[54] HYPOLIPIDEMIC AGENTS RO- OR RS-SUBSTITUTED FUROIC ACIDS, ESTERS AND SALTS

[75] Inventor: Roger Alan Parker, Cincinnati, Ohio

[73] Assignee: Richardson-Merrell Inc., Wilton, Conn.

[21] Appl. No.: 347,064

[22] Filed: Apr. 2, 1973

[51] Int. Cl.² .......................................... C07D 307/68
[52] U.S. Cl. ........................... 260/347.2; 260/293.67; 260/326.36; 260/347.3; 260/347.5; 424/248.52; 424/248.53; 424/248.55; 424/250; 424/267; 424/274; 424/285; 544/152; 544/379
[58] Field of Search ............. 260/347.2, 347.3, 347.5, 260/326.36, 293.67, 268 FT; 544/152

[56] References Cited
PUBLICATIONS

Burger, Medicinal Chemistry, part II, pp. 1123–1165 (third edition), (1970).
Manly, D. G. et al., "Jour. of Organic Chem.", vol. 21, pp. 516–519.

*Primary Examiner*—Richard L. Raymond
*Attorney, Agent, or Firm*—L. Ruth Hattan; Eugene O. Retter; George W. Rauchfuss, Jr.

[57] ABSTRACT

Substituted furoic acids and esters and pharmaceutically acceptable salts thereof of the following general structure are useful as hypolipidemic agents:

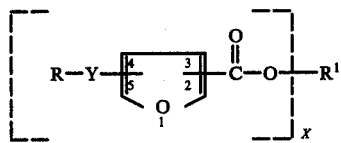

wherein Y represents oxygen or divalent sulfur; R represents a straight or branched alkyl chain containing from 10 to 20 carbon atoms and may be saturated or may be unsaturated containing from 1 to 4 double bonds; $R^1$ represents hydrogen, straight or branched lower alkyl of from 1 to 6 carbon atoms, benzyl, phenethyl, pyridylmethyl, alkane-poly-yl containing from 3 to 6 carbon atoms, 1,2,3,4,5,6-cyclohexanehexayl, or Z; Z represents (A) the group

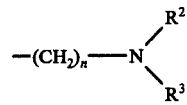

wherein $n$ is an integer of 2 or 3; $R^2$ represents straight or branched lower alkyl of from 1 to 4 carbon atoms, or acyl; $R^3$ represents hydrogen or straight or branched lower alkyl of from 1 to 4 carbon atoms with the proviso that when $R^3$ is hydrogen, $R^2$ is acyl; or when $R^2$ is other than acyl, $R^2$ and $R^3$ taken together with the nitrogen atom to which each is attached form a monocyclic heterocyclic group, such as pyrrolidino, piperidino, morpholino, or piperazino; or (B) the group

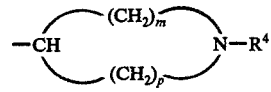

wherein the sum of the integers $m$ and $p$ is equal to from 3 to 5; and $R^4$ represents straight or branched lower alkyl of from 1 to 4 carbon atoms;

X is an integer of from 1 to 6 with the proviso that when $R^1$ is alkane-poly-yl or 1,2,3,4,5,6-cyclohexanehexayl, X is equal to from 2 to 6, and when $R^1$ is other than alkane-poly-yl or 1,2,3,4,5,6-cyclohexanehexayl, X is equal to 1.

12 Claims, No Drawings

HYPOLIPIDEMIC AGENTS RO- OR RS-SUBSTITUTED FUROIC ACIDS, ESTERS AND SALTS

FIELD OF INVENTION

This invention relates to substituted furoic acid and esters and pharmaceutically acceptable salts thereof and their use as hypolipidemic agents.

SUMMARY OF INVENTION

Compounds of the following general Formula 1 are useful as hypolipidemic agents:

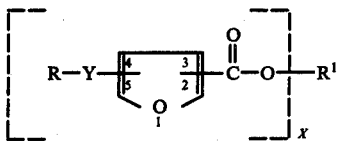

wherein Y represents oxygen or divalent sulfur; R represents a straight or branched alkyl chain containing from 10 to 20 carbon atoms which may be saturated or may be unsaturated containing from 1 to 4 double bonds; $R^1$ represents hydrogen, straight or branched lower alkyl of from 1 to 6 carbon atoms, benzyl, phenethyl, pyridylmethyl, alkane-poly-yl containing from 3 to 6 carbon atoms and from 2 to 6 univalent bonds, 1,2,3,4,5,6-cyclohexanehexayl, or Z; Z represents (A) the group

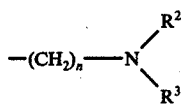

wherein $n$ is an integer of 2 or 3; $R^2$ represents straight or branched lower alkyl of from 1 to 4 carbon atoms or acyl; $R^3$ represents hydrogen or straight or branched lower alkyl of from 1 to 4 carbon atoms with the proviso that when $R^3$ is hydrogen, $R^2$ is acyl; or when $R^2$ is other than acyl, $R^2$ and $R^3$ taken together with the nitrogen atom to which each is attached form a monocyclic heterocyclic group such as pyrrolidino, piperidino, morpholino, or piperazino; or (B) the group

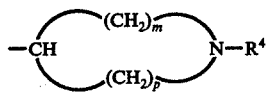

wherein the sum of the integers as represented by $m$ and $p$ is equal to from 3 to 5; and $R^4$ represents straight or branched lower alkyl of from 1 to 4 carbon atoms; X is an integer of from 1 to 6 with the proviso that when $R^1$ is alkane-poly-yl or 1,2,3,4,5,6-cyclohexanehexayl, X is equal to from 2 to 6, and when $R^1$ is other than alkane-poly-yl or 1,2,3,4,5,6-cyclohexanehexayl, X is equal to 1.

Pharmaceutically acceptable salts of compounds of Formula 1 wherein $R^1$ represents hydrogen or a basic group are also included within the scope of this invention.

DETAILED DESCRIPTION OF INVENTION

In the above general Formula 1 the substituent group represented as R—Y— may be attached at any of the positions 2-, 3-, 4-, or 5- of the furan ring. Illustrative examples of straight or branched saturated alkyl groups which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, 3-methyloctadecyl, nonadecyl and didecyl. Illustrative examples of straight or branched unsaturated alkyl groups containing from 1 to 4 double bonds which R may represent are, for example, 10-undecenyl, 9,12-octadecadienyl, 3,7,11-trimethyl-2,6,10-octatrienyl, 3,7-dimethyl-2,6-octadienyl, 5,9-dimethyl-2,4,8-decatrienyl, 3,7-dimethyloct-6-enyl, 1,2,5,9-tetramethyl-2,4,8-decatrienyl, and 11-didecenyl. Both the cis- and trans-isomers of the unsaturated alkyl groups are included within the scope of this invention.

Illustrative examples of straight or branched lower alkyl groups with $R^1$ may represent in general Formula 1 are, for example, methyl, ethyl, n-propyl, isopropyl, n-butyl, tert-butyl, pentyl and hexyl.

Illustrative examples of straight or branched lower alkyl groups which $R^2$, $R^3$ and $R^4$ may represent in the above general Formula 1 are, for example, methyl, ethyl, n-propyl, isopropyl, n-butyl and tert-butyl.

The term acyl is represented by $R^2$ in the above general Formula 1 is taken to mean an alkylcarbonyl radical wherein the alkyl moiety contains from 1 to 4 carbon atoms, such as methyl, ethyl, propyl and butyl.

The group alkane-poly-yl contains from 3 to 6 carbon atoms and from 2 to 6 univalent bonds. Illustrative examples of alkane-poly-yl groups which $R^1$ may represent in the above general Formula 1 are, for example, 1,3-propanediyl, 1,2,3-propanetriyl, 1,2-propanediyl, 1,2,3,4,5,6-hexanehexayl 1,5-pentanediyl, 1,6-hexanediyl.

The term 1,2,3,4,5,6-cyclohexanehexayl is taken to mean a cyclohexane radical with a univalent bond extending from each of the six carbon atoms.

Pharmaceutically acceptable salts of the compounds of general Formula 1 wherein $R^1$ represents hydrogen are those formed with any suitable inorganic or organic bases such as those of alkali metals, for example, sodium and potassium; alkaline earth metals, for example, calcium and magnesium, light metals of group III A, for example, aluminum; organic amines such as primary, secondary, or tertiary amines, for example, cyclohexylamine, ethylamine and piperidine. The salts can be prepared by conventional means such as by contacting and neutralizing a solution of a compound of Formula 1 having a carboxylic acid group in a polar solvent with the stoichiometric quantity of a base, for example, sodium hydroxide.

Pharmaceutically acceptable salts of the compounds of general Formula 1 wherein $R^1$ represents a basic group are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic maleic, hydroxymaleic, benzoic, hydroxybenzoic, phenylacetic, cinnamic, salicylic, 2-phenoxybenzoic and the like, or sulfonic acids such as, for example, methanesulfonic and 2-hydroxyethanesulfonic acid.

It is apparent from the above general Formula 1 that when $R^1$ is other than alkane-poly-yl or 1,2,3,4,5,6-cyclohexanehexayl the compounds are alkoxy- or alkylthiofuroic acid or monoester derivatives are represented by the following general Formula 11, or when $R^1$ is alkane-poly-yl or 1,2,3,4,5,6-cyclohexanehexayl the compounds are polyester derivatives of alkoxy- or alkylthiofuroic acid as represented by the following general Formula 111.

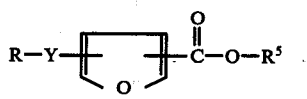

Formula II

In the above general Formula 11, Y represents oxygen or divalent sulfur; R represents a straight or branched alkyl chain containing from 10 to 20 carbon atoms and may be saturated or may be unsaturated containing from 1 to 4 double bonds; $R^5$ represents hydrogen, straight or branched lower alkyl of from 1 to 6 carbon atoms such as, for example, methyl, ethyl, propyl, isopropyl, tert-butyl and pentyl; benzyl, phenylethyl; pyridylmethyl; or Z; Z represents (A) the group

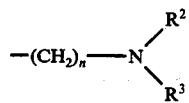

wherein n is an integer of 2 or 3; $R^2$ represents straight or branched lower alkyl of from 1 to 4 carbon atoms or acyl; $R^3$ represents hydrogen or straight or branched lower alkyl of from 1 to 4 carbon atoms with the proviso that when $R^3$ is hydrogen, $R^2$ is acyl; or when $R^2$ is other than acyl, $R^2$ and $R^3$ together with the nitrogen atom to which each is attached form a monocyclic heterocyclic group such as pyrrolidino, piperidino, morpholino or piperazino; or (B) the group

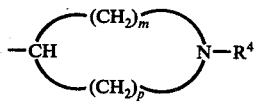

wherein the sum of the integers are represented by m and p is equal to from 3 to 5; and $R^4$ represents straight or branched lower alkyl of from 1 to 4 carbon atoms.

Formula III

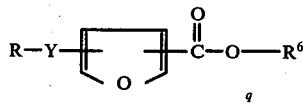

In the above general Formula 111, Y represents oxygen or divalent sulfur; R represents a straight or branched alkyl chain containing from 10 to 20 carbon atoms and may be saturated or may be unsaturated containing from 1 to 4 double bonds; $R^6$ represents alkane-poly-yl containing from 3 to 6 carbon atoms and from 2 to 6 univalent bonds, or 1,2,3,4,5,6-cyclohexanehexayl; q is an integer of from 2 to 6.

A preferred group of compounds of this invention are those of general Formula 1 wherein X is equal to 1; R and Y have the meanings as defined in general Formula 1; and $R^1$ represents hydrogen, straight or branched lower alkyl of from 1 to 4 carbon atoms, or Z wherein Z represents 4-(N-methyl)piperidyl, or the group

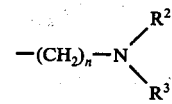

wherein n is equal to 2, and each of $R^2$ and $R^3$ represent lower alkyl of from 1 to 4 carbon atoms, or $R^2$ and $R^3$ taken together with the nitrogen atom to which each is attached forms a monocyclic heterocyclic group, such as, pyrrolidino, piperidino, morpholino or piperazino; and pharmaceutically acceptable salts thereof.

Illustrative examples of compounds of this invention are, for example, 5-decyloxy-2-furoic acid, 5-tetradecyloxy-2-furoic acid, 5-(trans-9-octadecenyloxy)-2-furoic acid, 5-dodecyloxy-2-furoic acid, 5-tetradecyloxy-2-furoic acid methyl ester, 5-tetradecyloxy-2-furoic acid ethyl ester, 5-octadecyloxy-2-furoic acid, 5-tetradecylthio-2-furoic acid, 4-dodecylthio-2-furoic acid butyl ester, 3-tridecyloxy-2-furoic acid benzyl ester, 5-hexadecyloxy-2-furoic acid methyl ester, 2-heptadecyloxy-3-furoic acid, 4-undecylthio-3-furoic acid ethyl ester, 5-hexadecyloxy-2-furoic acid diethylaminoethyl ester, 5-pentadecylthio-2-furoic acid 3-pyridylmethyl ester, 5-tetradecyloxy-2-furoic acid diester with 1,3-propanediol, 5-hexadecyloxy-2-furoic acid hexaester with inositol, 4-decyloxy-2-furoic acid triester with glycerol, 5-undecyloxy-2-furoic acid ethyl ester, 5-nonadecyloxy-2-furoic acid phenethyl ester, 5-didecyloxy-2-furoic acid propyl ester, 3-didecyloxy-2-furoic acid 4-pyridylmethylester, 4-dodecylthio-2-furoic acid dipropylaminopropyl ester, 5-tetradecyloxy-2-furoic acid piperidinoethyl ester, 4-hexadecyloxy-3-furoic acid morpholinoethyl ester, 5-undecyloxy-3-furoic acid 4-(N-methyl)piperidyl ester, 5-tetradecyloxy-2-furoic acid 3-pyrrolidinyl ester, 5-(10-undecenyloxy)-2-furoic acid, 4-(trans-trans-1,2,5,9-tetramethyl-2,4,8-decatrienyloxy)-2-furoic acid ethyl ester, 5-(cis-cis-9,12-octadienyloxy)-3-furoic acid benzyl ester, 5-(3,7-dimethyloct-6-enyloxy)-2-furoic acid.

The compounds of this invention are useful as hypolipidemic agents in that they reduce blood lipids, particularly cholesterol and triglycerides without concurrent accumulation of desmosterol. These compounds can be administered to animals, mammals and humans and are useful in the treatment of hyperlipidemic states such as are encountered in patients with cardiovascular diseases that can result in heart failure and stroke.

To illustrate the utility of the compounds of this invention young male rats of the Wistar strain initially weighing about 175 grams were given free access to a diet which contained 0.15% by weight of test compound, that is, a compound of general Formula 1. This diet was prepared by mixing the test compound with commercial Purina Chow. (Trademark of Ralston Purina Company, St. Louis, Missouri). Groups of animals were given these diets for either 4 or 10 days. Control groups of 6 rats each were given Purina Chow to which no test compound had been added. At the end of the treatment period all rats were bled by cardiac puncture, and the plasma was analyzed for cholesterol and triglyceride content. The results are given in the following Table 1.

TABLE 1

| Test Compound | Duration Treatment (Days) | Daily Dose mg/kg (a) | No. Rats | Plasma Cholesterol % Reduction (b) | Plasma Triglycerides % Reduction (b) |
| --- | --- | --- | --- | --- | --- |
| 5-Decyloxy-2-furoic acid | 4 | 145 | 6 | 5 | 46 |
| 5-Tetradecyloxy-2-furoic acid | 4 | 133 | 6 | 40 | 75 |
| 5-Hexadecyloxy-2-furoic acid | 4 | 154 | 6 | 24 | 25 |
| 5-Tetradecyloxy-2-furoic acid methyl ester | 4 | 150 | 6 | 32 | 67 |
| 5-Tetradecyloxy-2-furoic acid ethyl ester | 4 | 156 | 6 | 30 | 64 |
| 5-Octadecyloxy-2-furoic acid | 4 | 160 | 6 | 18 | 53 |
| 5-Tetradecylthio-2-furoic acid | 4 | 151 | 6 | 18 | 63 |

(a) Determined by measuring food consumption.
(b) Compared to untreated control rats in the same experiment.

The compounds of this invention can be administered orally or parenterally either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.5 mg/kg (milligrams per kilogram) to about 100 mg/kg of body weight of the patient per day, and preferably from about 10 mg/kg to 30 mg/kg of body weight of the patient per day, to achieve the desired effect. Unit doses can contain from about 50 mg to 1 g of a compound of this invention and may be administered, for example from 1 to 4 times daily.

The compounds of general Formula I wherein $R^1$ is hydrogen are prepared by aromatic nucleophilic substitution [J. March, *Advanced Organic Chemistry: Reactions, Mechanisms, and Structures*, McGraw-Hill, p. 500(1968)] as outlined below.

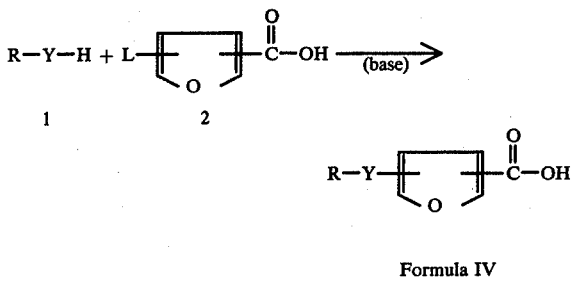

In the above general reaction Y represents oxygen or divalent sulfur; R represents a straight or branched alkyl chain containing from 10 to 20 carbon atoms which may be saturated or may be unsaturated containing from 1 to 4 double bonds; L represents a leaving group such as nitro, chloro, bromo, or iodo, the preferred leaving group being bromo. The substituent group L on compound 2 and R-Y- on compounds of Formula IV may be attached at the 2-, 3-, 4-, or 5-position of the furan ring and the

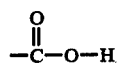

group may be attached at the 2- or 3- position with the proviso that both L or R-Y- and

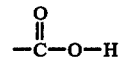

are not attached at the same position of the furan ring.

The above reaction may be carried out with or without a solvent. Suitable solvents for the reaction include benzene, xylene, toluene, chlorinated aromatic hydrocarbons such as chlorobenzene, ethers such as bis(2-methoxyethyl)ether, 1,2-dimethoxyethane or anisole, dimethyl formamide, dimethyl acetamide, 1-methyl-2-pyrrolidone or pyridine. Preferred solvents are dimethyl formamide and dimethyl acetamide. Copper metal or a salt such as cuprous chloride may optionally be added to the reaction. Suitable bases for the reaction include sodium or potassium metal, sodium hydride, potassium amide, potassium tert-butylate or other strong bases, such as, potassium carbonate potassium hydroxide, sodium hydroxide and sodium carbonate. The temperature of the reaction varies from about room temperature to reflux temperature of the solvent, and the reaction time varies from about 1 hour to about 7 days.

Alcohols as represented by compound 1 which find use in the above general reaction are commercially available or may be prepared by reduction of the corresponding carboxylic acid or aldehyde. The furoic acid derivatives as represented by compound 2 may be prepared by several methods as described in *The Furans*, by A. P. Dunlop and F. N. Peters, Reinhold Publishing Corp., pp. 80 to 169 (1953).

Esterification of the furoic acids as represented by the above general Formula IV to give compounds of general Formula I wherein $R^1$ is other than hydrogen may be carried out by several methods. For example, compounds of Formula IV are converted to the metal salt, for example, sodium or potassium or an amine salt, for example, ammonium salt or triethylammonium salt and subsequently reacted with an alkyl halide of the formula halo-$R^1$ or an alkylsulfate of the formula $R^1SO_4R^1$ or a sulfonate of the formula $R^1OSOR^7$ wherein $R^1$ has the meaning defined in general Formula I except that $R^1$ is not hydrogen, and $R^7$ is lower alkyl of from 1 to 4 carbon atoms or substituted aryl, for example, tosyl. Esterification of compounds of general Formula IV may also be carried out by alcoholysis of the substituted furoic acid chloride, which is formed by reacting the acid with the thionyl chloride, or of the substituted furoic acid imidazolide, which is formed by reacting the acid with N,N'-carbonyldiimidazole, with an alcohol of the formula $R^1$—OH wherein $R^1$ has the meaning defined in general Formula I except that $R^1$ is not hydrogen. Esterification may also be promoted by the reaction of a substituted furoic acid compound of general Formula IV with an alcohol of the formula R¹—OH wherein R¹ has the meaning defined in general Formula I except that R¹ is not hydrogen and a dehydrating agent, for example, N,N'-dicyclohexylcarbodiimide.

The following specific examples are illustrative of the invention.

EXAMPLE 1

5-Decyloxy-2-furoic acid

A mixture of 30.0 g (0.157 mole) of 5-bromofuroic acid, 75.4 g (0.471 mole) of decanol and 1000 ml of dried dimethyl acetamide is stirred at room temperature after which 15.0 g (0.628 mole) of sodium hydride is added. The mixture is refluxed with stirring for 42 hours after which the mixture is poured into a water-ice mixture, acidified with acetic acid and extracted with ether. The ether layer is washed several times with water and salt water, then dried over sodium sulfate, filtered and evaporated on a steam bath replacing the ether with hexane and allowing the mixture to crystallize. The solid obtained is recrystallized from methanol to give 5-decyloxy-2-furoic acid, M.P. 124°–126° C.

EXAMPLE 2

5-Tetradecyloxy-2-furoic acid

When in Example 1 tetradecanol is substituted for decanol and the reaction mixture is refluxed with stirring for 20 hours, 5-tetradecyloxy-2-furoic acid, M.P. 112°–115° C, is obtained.

EXAMPLE 3

5-Hexadecyloxy-2-furoic acid

When in Example 1 hexadecanol is substituted for decanol, 5-hexadecyloxy-2-furoic acid, M.P. 118°–119° C, is obtained.

EXAMPLE 4

5-(cis-9-Octadecenyloxy)-2-furoic acid

A mixture of 30.0 g (0.157 mole) of 5-bromofuroic acid, 43.7 g (0.157 mole) of oleylalcohol and 500 ml of dried dimethylformamide is flushed with nitrogen and stirred at room temperature after which 7.55 g (0.314 mole) of sodium hydride is added. The mixture is stirred at room temperature for an hour then heated to reflux. The mixture is refluxed for 92 hours after which the mixture is poured into an ice-water mixture, acidified with acetic acid and extracted with ether. The ether layer is washed with water and salt water, dried over sodium sulfate, filtered ane evaporated replacing the ether with hexane. Upon cooling a solid is formed which is recrystallized from methanol to give 5-(cis-9octadecenyloxy)-2-furoic acid, M.P. 93°–96° C.

EXAMPLE 5

5-Dodecyloxy-2-furoic acid

A mixture of 30.0 g (0.157 mole) of 5-bromofuroic acid, 29.4 g (0.157 mole) of dodecanol and 500 ml of pyridine is flushed with nitrogen and stirred at room temperature after which 7.55 g (0.314 mole) of sodium hydride is added. The mixture is heated to 100° C for 20 hours, then refluxed 1 hour after which 2.0 g of cuprous chloride is added. The mixture is refluxed with stirring under nitrogen for 20 hours, then poured into an ice-water-hydrochloric acid mixture with stirring and filtered. The resulting oily precipitate is extracted into ether, washed with 5% hydrochloric acid solution, water and salt water, dried over sodium sulfate, filtered, and evaporated on a steam bath replacing the ether with hexane. The solid obtained is recrystallized from methanol to give 5-dodecyloxy-2-furoic acid, M.P. 122°–123° C.

EXAMPLE 6

5-Tetradecyloxy-2-furoic acid methyl ester

A mixture of 10.0 g of (0.031 mole) of 5-tetradecyloxy-2-furoic acid, 200 ml of acetone and 4.3 g (0.031 mole) of potassium carbonate is stirred at room temperature after which 3.9 g (0.031 mole) of dimethylsulfate is added. The mixture is stirred with heating for about two and one-half hours during which time 10 ml of methanol is added. The mixture is then diluted with 100 ml of acetone, and filtered. The filtrate is evaporated to dryness and recrystallized from methanol to give 5-tetradecyloxy-2-furoic acid methyl ester, M.P. 56°–58° C.

EXAMPLE 7

5-Tetradecyloxy-2-furoic acid ethyl ester

A mixture of 10.0 g (0.031 mole) of 5-tetradecyloxy-2-furoic acid, 4.3 g (0.034 mole) of potassium carbonate, and dimethyl formamide is stirred at room temperature after which 15.6 g (0.10 mole) of ethyl iodide is added. The mixture is heated to 50° C with stirring overnight then poured into water and extracted with ether. The ether layer is washed with water and salt water then dried over sodium sulfate, filtered, and the ether is distilled off and replaced by ethanol. Upon cooling the ethanol solution a solid is obtained which is 5-tetradecyloxy-2-furoic acid ethyl eseter, M.P. 39°–40° C.

EXAMPLE 8

5-Octadecyloxy-2-furoic acid

A mixture of 30.0 g (0.157 mole) of 5-bromofuroic acid, 64.0 g (0.236 mole) of octadecanol and 500 ml of bis(2-methoxyethyl)ether is stirred at room temperature under nitrogen after which 9.45 g (0.393 mole) of sodium hydride is added. The mixture is refluxed about 22 hours, allowed to cool and poured into an ice-water mixture, acidified with acetic acid and extracted with ether. The ether layer is washed with water and salt water, dried over sodium sulfate, and filtered. The solvent is evaporated off replacing the ether with hexane. Upon cooling to room temperature a solid forms which is recrystallized from methanol to give 5-octadecyloxy-2-furoic acid, M.P. 117°–118° C.

EXAMPLE 9

5-Tetradecylthio-2-furoic acid

A mixture of 20.1 g (0.011 mole) of 5-bromofuroic acid, 24.2 g (0.011 mole) of tetradecanethiol in 800 ml of dimethylformamide and 8.5 g (0.021 mole) of sodium hydride is heated on a steam bath overnight then refluxed for one-half hour. The mixture is then cooled, acidified with acetic acid and extracted with ether-water. The ether layer is washed with water and salt water, dried over sodium sulfate and filtered. The filtrate is evaporated to dryness, and the remaining solid is recrystallized from hexane and from methanol to give 5-tetradecylthio-2-furoic acid, M.P. 84°–86° C.

When in Example 1 an alcohol listed below is substituted for decanol, and a furoic acid listed below is employed, the respective products are obtained.

| Ex. No. | Product | Alcohol | Furoic Acid |
|---|---|---|---|
| 10 | 2-didecyloxy-3-furoic acid | didecanol | 2-bromo-3-furoic acid |
| 11 | 5-heptadecyloxy-3-furoic acid | heptadecanol | 5-bromo-3-furoic acid |
| 12 | 5-decylthio-2-furoic acid | decanethiol | 5-nitro-2-furoic acid |
| 13 | 4-hexadecylthio-2-furoic acid | hexadecanethiol | 4-bromo-2-furoic acid |
| 14 | 5-(10-undecenyloxy)-2-furoic acid | 10-undecen-1-ol | 5-bromo-2-furoic acid |
| 15 | 5-(trans-3,7-dimethyl-2,6-octadienyloxy)-3-furoic acid | trans-3,7-dimethyl-2,6-octadien-1-ol | 5-bromo-2-furoic acid |
| 16 | 5-(cis-cis-9,12-octadecadienyloxy)-2-furoic acid | cis-cis-9,12-octadecadien-1-ol | 5-bromo-2-furoic acid |
| 17 | 5-(trans-trans-3,7,11-trimethyl-2,6,10-dodecatrienyloxy)-2-furoic acid | trans-trans-3,7,11-trimethyl-2,6,10-dodecatrien-1-ol | 5-bromo-2-furoic acid |
| 18 | 5-(trans-3,7-dimethyl-2,6-octadienyloxy)-2-furoic acid | trans-3,7-dimethyl-2,6-octadien-1-ol | 5-bromo-2-furoic acid |

EXAMPLE 19

5-Tetradecyloxy-2-furoic acid benzyl ester

When in Example 7 benzyl chloride is substituted for ethyl iodide, 5-tetradecyloxy-2-furoic acid benzyl ester is obtained.

EXAMPLE 20

When in Example 7, 5-decyloxy-2-furoic acid, 5-tetradecylthio-2-furoic acid and 5-hexadecyloxy-2-furoic acid are each substituted for 5-tetradecyloxy-2-furoic acid, and diethylaminoethyl bromide, pyridylmethyl bromide and piperidinoethyl bromide are each respectively substituted for ethyl iodide the following respective products are obtained:

5-decyloxy-2-furoic acid diethylaminoethyl ester,
5-tetradecylthio-2-furoic acid pyridylmethyl ester,
5-hexadecyloxy-2-furoic acid piperidinoethyl ester.

EXAMPLE 21

5-Tetradecyloxy-2-furoic acid triester with 1,2,3-propanetriol

A mixture of 3 equivalents of 5-tetradecyloxy-2-furoic acid, 1 equivalent of 1,2,3-propanetriol and 3 equivalents of N,N'-dicyclohexyldicarbodiimide in ether is stirred at room temperature for about 3 days after which the mixture is filtered. The filtrate is washed with water, dried over sodium sulfate, filtered and evaporated to dryness to give 5-tetradecyloxy-2-furoic acid triester with 1,2,3-propanetriol.

EXAMPLE 22

5-Dodecyloxy-2-furoic acid hexaester with inositol

When in Example 21, 6 equivalents of 5-dodecyloxy-2-furoic acid is substituted for 5-tetradecyloxy-2-furoic acid, 1 equivalent of inositol is substituted for 1,2,3-propanetriol, and 6 equivalents of N,N'-dicyclohexyldicarbodiimide is used, 5-dodecyloxy-2-furoic acid hexaester with inositol is obtained.

EXAMPLE 23

5-Tetradecyloxy-2-furoic acid sodium salt

To 19.5 g (0.06 mols) of 5-tetradecyloxy-2-furoic acid in 500 ml of methanol is added 6 g (0.111 mole) of sodium methoxide. The mixture is refluxed, and the methanol is distilled off being replaced by water. The aqueous solution is cooled, the precipitate collected and dried to give 5-tetradecyloxy-2-furoic acid sodium salt, M.P. 240°–245° C (dec.).

EXAMPLE 24

An illustrative composition for tablets is as follows:

|   |   | Per Tablet |
|---|---|---|
| (a) | 5-tetradecyloxy-2-furoic acid ethyl ester | 100.0 mg |
| (b) | wheat starch | 15.0 mg |
| (c) | lactose | 33.5 mg |
| (d) | magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 25

An illustrative composition for a parenteral injection is the following wherein the quantities are on a weight to volume basis.

|   |   | Amount |
|---|---|---|
| (a) | 5-tetradecyloxy-2-furoic acid sodium salt | 100.0 mg |
| (b) | sodium chloride | q.s. |
| (c) | water for injection to make | 20.0 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

EXAMPLE 26

An illustrative composition for hard gelatin capsules is as follows:

|   |   | Amount |
|---|---|---|
| (a) | 5-hexadecyloxy-2-furoic acid | 200.0 mg |
| (b) | talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

I claim:

1. A compound of the formula

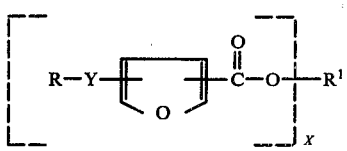

wherein Y is selected from oxygen or divalent sulfur; R is selected from a straight or branched alkyl chain containing from 10 to 20 carbon atoms which may be saturated or may be unsaturated containing from 1 to 4 double bonds; $R^1$ is selected from hydrogen, a straight or branched lower alkyl group of from 1 to 6 carbon atoms, benzyl, phenethyl, pyridylmethyl, alkan-poly-yl containing from 3 to 6 carbon atoms and from 2 to 6 univalent bonds, 1,2,3,4,5,6-cyclohexanehexayl or Z; Z is selected from:

(A) the group:

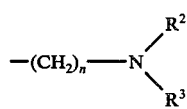

wherein $n$ is an integer of 2 or 3; $R^2$ is selected from a straight or branched lower alkyl group of from 1 to 4 carbon atoms or an alkylcarbonyl radical wherein the alkyl moiety contains from 1 to 4 carbon atoms; $R^3$ is selected from hydrogen, a straight or branched lower alkyl group of from 1 to 4 carbon atoms with the proviso that when $R^3$ is hydrogen, $R^2$ is alkylcarbonyl; or when $R^2$ is other than alkylcarbonyl, $R^2$ and $R^3$ taken together with the nitrogen atom to which each is attached from a monocyclic heterocyclic group selected from pyrrolidino, piperidino, morpholino and piperazino; or (B) the group:

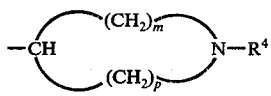

wherein the sum of the integers as represented by $m$ and $p$ is equal to from 3 to 5; $R^4$ is selected from a straight or branched lower alkyl chain of from 1 to 4 carbon atoms; X is an integer of from 1 to 6 with the proviso that when $R^1$ is selected from alkan-poly-yl, X is equal to from 2 to 6 and when $R^1$ is 1,2,3,4,5,6-cyclohexanehexayl, X is equal to 6, and when $R^1$ is selected from other than alkanpoly-yl and 1,2,3,4,5,6-cyclohexanehexayl, X is equal to 1; or a pharmaceutically acceptable salt thereof.

2. A compound of the formula:

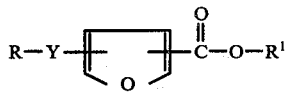

wherein Y is selected from oxygen or divalent sulfur; R is selected from a straight or branched alkyl chain containing from 10 to 20 carbon atoms which may be saturated or may be unsaturated containing from 1 to 4 double bonds; $R^1$ is selected from hydrogen, a straight or branched lower alkyl group of from 1 to 6 carbon atoms, benzyl, phenethyl, pyridylmethyl or Z; Z is selected from:

(A) the group:

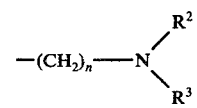

wherein $n$ is an integer of 2 or 3; $R^2$ is selected from a straight or branched lower alkyl group of 1 to 4 carbon atoms or an alkylcarbonyl radical wherein the alkyl moiety contains from 1 to 4 carbon atoms; $R^3$ is selected from hydrogen, a straight or branched lower alkyl group of from 1 to 4 carbon atoms with the proviso that when $R^3$ is hydrogen, $R^2$ is alkylcarbonyl; or when $R^2$ is other than alkylcarbonyl, $R^2$ and $R^3$ taken together with the nitrogen atom to which each is attached form a monocyclic heterocyclic group selected from pyrrolidino, piperidino, morpholino and piperazino; or (B) the group:

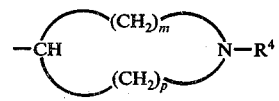

wherein the sum of the integers as represented by $m$ and $p$ is equal to from 3 to 5; $R^4$ is selected from a straight or branched lower alkyl chain of from 1 to 4 carbon atoms; or a pharmaceutically acceptable salt thereof.

3. A compound of claim 1 wherein $R^1$ is selected from hydrogen, a straight or branched lower alkyl group of from 1 to 6 carbon atoms, benzyl, phenethyl, alkanepoly-yl containing from 3 to 6 carbon atoms and from 2 to 6 univalent bonds, or 1,2,3,4,5,6-cyclohexanehexayl.

4. A compound of claim 3 wherein the group R—Y— is attached to the 4- or 5-position of the furan ring and the group

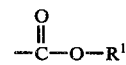

is attached to the 2-position of the furan ring.

5. A compound of claim 4 wherein $R^1$ is selected from hydrogen, a straight or branched lower alkyl group of from 1 to 6 carbon atoms, benzyl or phenethyl.

6. A compound of claim 1 wherein $R^1$ is selected from 4-(N-methyl)piperidyl, pyridylmethyl, or the group

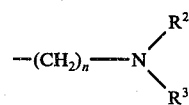

wherein $n$ is equal to 2; each of $R^2$ and $R^3$ is selected from a straight or branched lower alkyl group of from 1 to 4 carbon atoms; or $R^2$ and $R^3$ taken together with the nitrogen atom to which each is attached form a monocyclic heterocyclic group selected from pyrrolidino, piperidino, morpholino or piperazino.

7. A compound of claim 5 which is 5-dodecyloxy-2-furoic acid and pharmaceutically acceptable salts thereof.

8. A compound of claim 5 which is 5-tetradecyloxy-2-furoic acid and pharmaceutically acceptable salts thereof.

9. A compound of claim 5 which is 5-octadecyloxy-2-furoic acid and pharmaceutically acceptable salts thereof.

10. A compound of claim 5 which is 5-tetradecyloxy-2-furoic acid methyl ester.

11. A compound of claim 5 which is 5-tetradecyloxy-2-furoic acid ethyl ester.

12. A compound of claim 5 which is 5-tetradecylthio-2-furoic acid and pharmaceutically acceptable salts thereof.

* * * * *